United States Patent [19]
Huff et al.

[11] Patent Number: 6,111,159
[45] Date of Patent: Aug. 29, 2000

[54] HYDROCARBON CONVERSION PROCESS

[75] Inventors: George A. Huff, Naperville, Ill.;
Anthony M. Valente, Yorktown, Va.;
Robert L. Mehlberg, Wheaton, Ill.;
David B. Johnson, Hayes, Va.

[73] Assignee: BP Amoco Corporation, Chicago, Ill.

[21] Appl. No.: 09/203,019

[22] Filed: Dec. 1, 1998

[51] Int. Cl.[7] .............................. C07C 2/68; C07C 2/24; C07C 2/02
[52] U.S. Cl. ........................ 585/529; 585/466; 585/514
[58] Field of Search ................... 585/509, 514, 585/524, 406, 466; 528/486, 441, 447, 503

[56] References Cited

U.S. PATENT DOCUMENTS

| | | | |
|---|---|---|---|
| 2,120,702 | 6/1938 | Ipatieff et al. | 23/233 |
| 3,050,472 | 8/1962 | Morrell | 252/435 |
| 3,050,473 | 8/1962 | Morrell | 252/435 |
| 3,132,109 | 5/1964 | Morrell | 252/435 |
| 3,887,634 | 6/1975 | Hughes | 260/683.15 C |
| 4,334,118 | 6/1982 | Manning | 585/529 |

FOREIGN PATENT DOCUMENTS 863539  3/1961  United Kingdom .

OTHER PUBLICATIONS

P.C. Weinert et al., "Catalytic Polymerization and Its Commercial Application," *Petroleum Processing*, Jun. 1948) pp. 585–593.

W.F. Deeter, "Propylene Polymerization for Motor–Gasoline Production," *The Oil and Gas Journal*, (Mar. 23, 1950) pp. 252–258.

G.E. Langlois et al., "An Improved Process for Polymerization of Olefins with Phosphoric Acid on Quartz Catalyst," *Proceedings Third World Petroleum Congress—Section IV*, (1951) pp. 191–200.

G. Egloff et al., "Polymerisation with Solid Phosphoric Acid Catalyst," *Proceedings Third World Petroleum Congress—Section IV*, (1951) pp. 201–214.

E.K. Jones, "Polymerization of Olefins from Cracked Gases," *Advances in Catalysis*, vol. VIII, Academic Press Inc., New York, N.Y., (1956) pp. 219–238.

J. Villadsen et al., "Supported Liquid–Phase Catalysts," *Catal. Rev.—Sci. Eng.*, (1978) pp. 226–228.

F. Cavani et al., "Effect of Water in the Performance of the 'Solid Phosphoric Acid' Catalyst for Alkylation of Benzene to Cumene and for Oligomerization of Propene," *Applied Catalysis A: General*, 97 (1993) pp. 177–196.

*Primary Examiner*—Jacqueline V. Howard
*Assistant Examiner*—Thuan D. Dang
*Attorney, Agent, or Firm*—Richard A. Kretchmer

[57] ABSTRACT

A method is provided for putting a fresh bed of solid phosphoric acid catalyst into service to catalyze a hydrocarbon conversion process. The method involves establishing hydrocarbon conversion conditions of temperature and pressure in the catalyst bed while it is immersed in a hydrocarbon liquid which is substantially free of water and compounds which can yield water upon contact with the catalyst. Thereafter, the catalyst bed is used to catalyze the conversion of a hydrocarbon feedstock which contains a minor amount of a hydrating agent which is effective to provide a desired level of catalyst hydration. The method permits the catalyst to be rapidly brought to an optimum level of activity for the specific hydrocarbon conversion process.

25 Claims, No Drawings ized as a polymerization or an alkylation process, will be a
function of the degree of catalyst hydration. In an olefin
polymerization process, a properly hydrated solid phosphoric acid catalyst can be used to convert over 95% of the
olefins in a feedstock to higher molecular weight products.
However, if the catalyst contains too little water, it tends to
have a very high acidity, which can lead to rapid deactivation as a consequence of coking, and the catalyst will not
possess a good physical integrity. Further hydration of the
catalyst serves to reduce its acidity and reduces its tendency
toward rapid deactivation through coke formation. However,
excessive hydration of a solid phosphoric acid catalyst can
cause the catalyst to soften and physically agglomerate and,
as a consequence, can create high pressure drops in fixed bed
reactors. Accordingly, there is an optimum level of hydration
for a solid phosphoric acid catalyst.

HYDROCARBON CONVERSION PROCESS

FIELD OF THE INVENTION

This invention relates to a process for initiating and
sustaining a hydrocarbon conversion process over a fixed
bed of solid phosphoric acid catalyst. More specifically, the
invention is an improved method for initiating and sustaining such a process which is capable of rapidly bringing the
catalyst to peak activity.

BACKGROUND OF THE INVENTION

The condensation reaction of an olefin or a mixture of
olefins over an acid catalyst to form higher molecular weight
products is a widely used commercial process. This type of
condensation reaction is referred to herein as a polymerization reaction, and the products can be either low molecular
weight oligomers or high molecular weight polymers. Oligomers are formed by the condensation of 2, 3 or 4 olefin
molecules with each other, while polymers are formed by the
condensation of 5 or more olefin molecules with each other.
As used herein, the term "polymerization" is used to refer to
a process for the formation of oligomers and/or polymers.
Low molecular weight olefins (such as propene,
2-methylpropene, 1-butene and 2-butene) can be converted
by polymerization over a solid phosphoric acid catalyst to a
product which is comprised of oligomers and is of value as
a high-octane gasoline blending stock and as a starting
material for the production of chemical intermediates and
end-products which include alcohols, detergents and plastics.

The acid catalyzed alkylation of aromatic compounds
with olefins is a well-known reaction which is also of
commercial importance. For example, ethylbenzene,
cumene and detergent alkylate are produced by the alkylation of benzene with ethylene, propene and $C_{10}$ to $C_{18}$
olefins, respectively. Sulfuric acid, HF, phosphoric acid,
aluminum chloride, and boron fluoride are conventional
catalysts for this reaction. In addition, solid acids which
have comparable acid strength can also be utilized to catalyze this process, and such materials include amorphous and
crystalline aluminosilicates, clays, ion-exchange resins,
mixed oxides and supported acids such as solid phosphoric
acid catalysts.

Solid phosphoric acid catalysts are typically prepared by
combining a phosphoric acid with a support and drying the
resulting material. A commonly used catalyst is prepared by
mixing kieselguhr with phosphoric acid, extruding the
resulting paste, and calcining the extruded material. The
activity of a solid phosphoric acid catalyst is related to the
amount and the chemical composition of the phosphoric acid
which is deposited on the support. Phosphoric acid consists
of a family of acids which exist in equilibrium with each
other and differ from each other in their degree of condensation. These acids include ortho-phosphoric acid ($H_3PO_4$),
pyro-phosphoric acid ($H_4P_2O_7$), triphosphoric acid
($H_5P_3O_{10}$), and polyphosphoric acids, and the precise composition of a given sample of phosphoric acid will be a
function of the $P_2O_5$ and water content of the sample. As the
water content of the acid decreases, the degree of condensation of the acid increases. Each of the various phosphoric
acids has a unique acid strength, and, accordingly, the
catalytic activity of a given sample of solid phosphoric acid
catalyst will depend on the $P_2O_5/H_2O$ ratio of the phosphoric acid which is deposited on the surface of the catalyst.

The activity of a solid phosphoric acid catalyst and also its
rate of deactivation in a hydrocarbon conversion process, During use as a catalyst for a hydrocarbon conversion
process, a solid phosphoric acid catalyst will develop a
degree of hydration which is a function of feedstock composition and reaction conditions. For example, the level of
hydration is affected by the water content of the feedstock
which is being contacted with the catalyst and also by the
temperature and pressure at which the catalyst is used. The
vapor pressure of water over a solid phosphoric acid catalyst
varies with temperature, and it is important to keep the water
content of the hydrocarbon process stream in equilibrium
with that of the catalyst it is being contacted with. If a
substantially anhydrous hydrocarbon feedstock is used with
a properly hydrated catalyst, the catalyst will typically loose
water during use and will develop a less than optimal degree
of hydration. Accordingly, when the water content of a
feedstock is inadequate to maintain an optimal level of
catalyst hydration, it has been conventional to inject additional water into the feedstock. A study of the effect of water
on the performance of solid phosphoric acid catalyst as a
catalyst for the alkylation of benzene with propene and for
the oligomerization of propene is set forth in a review article
by Cavani et al., *Applied Catalysis A: General*, 97, pp.
177–196 (1993).

As an alternative to incorporating water into a feedstock
that is being contacted with a solid phosphoric acid catalyst,
it is also conventional practice to add a small amount of an
alcohol, such as 2-propanol, to the feedstock to maintain the
catalyst at a satisfactory level of hydration. For example,
U.S. Pat. No. 4,334,118 (Manning) discloses that in the
polymerization of $C_3$–$C_{12}$ olefins over a solid phosphoric
acid catalyst which has a siliceous support, the catalyst
activity can be maintained at a desirable level by including
a minor amount of an alkanol in the olefin feedstock. It is
also disclosed that the alcohol undergoes dehydration upon
contact with the catalyst, and that the resulting water then
acts to maintain the catalyst hydration.

SUMMARY OF THE INVENTION

A commercial solid phosphoric acid catalyst does not
ordinarily have an optimal degree of hydration when it is
initially put into service as a catalyst in a hydrocarbon
conversion process. This can result from a number of
problems which may include, among others, adsorption of
atmospheric moisture before the catalyst can be put into
service and the fact that a generic catalyst is manufactured
for use under a variety of different process conditions and
with different feedstocks. As a result, when a fresh bed of
solid phosphoric acid catalyst is put into service as a catalyst
in a hydrocarbon conversion process, it will typically take a
number of days before optimum catalyst performance is
observed. For example, when a fresh bed of solid phosphoric acid catalyst is put into service to catalyze the polymerization of a mixture of propene and $C_4$ olefins, it can take more than 10 days of continuous operation before the catalyst performance reaches an optimal level.

We have discovered a method for putting a fresh bed of solid phosphoric acid catalyst into use which reduces the amount of time required to optimize the catalyst performance for a given hydrocarbon feedstock and set of process conditions. Our invention involves establishing hydrocarbon conversion conditions in the catalyst bed without exposing the catalyst to any significant source of water and, thereafter, using the catalyst bed to catalyze the conversion of a hydrocarbon feedstock which contains a minor amount of a hydrating agent which is effective to provide the desired level of catalyst hydration.

One embodiment of the invention is a process for the chemical conversion of a hydrocarbon feedstock over a fixed bed of solid phosphoric acid catalyst which comprises:

(a) immersing the bed of catalyst in a start-up fluid, wherein said start-up fluid is comprised of a hydrocarbon liquid which is substantially free of water and compounds which can yield water upon contact with the catalyst;

(b) establishing conversion conditions of temperature and pressure in the catalyst bed while the catalyst bed is immersed in the start-up fluid;

(c) replacing the start-up fluid with the hydrocarbon feedstock and passing said feedstock through the catalyst bed under said conversion conditions, wherein the feedstock contains a minor amount of a hydrating agent which is comprised of at least one material selected from the group consisting of water and monohydric aliphatic alcohols which contain from 2 to 12 carbon atoms, and wherein the amount of said hydrating agent is effective to provide a desired level of catalyst hydration; and (d) maintaining the flow of said feedstock through the catalyst bed under said conversion conditions.

Another embodiment of the invention is an olefin polymerization process carried out over a fixed bed of solid phosphoric acid catalyst which comprises:

(a) immersing the bed of catalyst in a start-up fluid, wherein said start-up fluid is comprised of a hydrocarbon liquid which is substantially free of water and compounds which can yield water upon contact with the catalyst;

(b) establishing olefin polymerization conditions of temperature and pressure in the catalyst bed while the catalyst bed is immersed in the start-up fluid;

(c) replacing the start-up fluid with an olefin-containing feedstock and passing said feedstock through the catalyst bed under said polymerization conditions, wherein the feedstock contains a minor amount of a hydrating agent which is comprised of at least one material selected from the group consisting of water and monohydric aliphatic alcohols which contain from 2 to 12 carbon atoms, and wherein the amount of said hydrating agent is effective to provide a desired level of catalyst hydration; and (d) maintaining the flow of said feedstock through the catalyst bed under said polymerization conditions.

An object of the invention is an improved process for the chemical conversion of a hydrocarbon feedstock over a fixed bed of solid phosphoric acid catalyst.

An object of the invention is an improved process for the polymerization of olefins over a fixed bed of solid phosphoric acid catalyst.

An object of the invention is to provide an improved process for putting a fixed bed of solid phosphoric acid catalyst into service as a hydrocarbon conversion catalyst.

An object of the invention is to provide an improved process for putting a fixed bed of solid phosphoric acid catalyst into service as an olefin polymerization catalyst.

Another object of the invention is to provide a method for rapidly bringing a fixed bed of fresh solid phosphoric acid catalyst to a desired level of activity when put into service as a hydrocarbon conversion catalyst.

A further object of the invention is to provide a method for rapidly bringing a fixed bed of fresh solid phosphoric acid catalyst to a desired level of activity when put into service as an olefin polymerization catalyst.

DETAILED DESCRIPTION OF THE INVENTION

The present invention relates to a process for putting a fixed bed of solid phosphoric acid into service to catalyze the chemical conversion of a hydrocarbon feedstock. The invention permits the catalyst to be rapidly brought to an optimum level of activity for the specific hydrocarbon conversion process. Although the invention is not to be so limited, it is believed that the process of this invention produces a rapid adjustment of the catalyst hydration to the level required for optimum catalyst activity.

This invention can be used in the practice of any conventional hydrocarbon conversion process which is carried out over a solid phosphoric acid catalyst. Such processes include, but are not limited to, the polymerization of olefins and the alkylation of aromatics with olefins. Specific examples of such processes include the oligomerization of $C_3$ and $C_4$ olefins to liquids which are useful as gasoline blending stocks, the preparation of a $C_{12}$–$C_{15}$ olefinic mixture which is useful as a chemical feedstock by polymerizing four or five molecules of propene, the preparation of ethylbenzene by alkylation of benzene with ethylene, and the synthesis of cumene by alkylation of benzene with propene.

In the practice of the invention, the fixed bed of solid phosphoric acid catalyst is initially immersed in a start-up fluid which is comprised of a hydrocarbon liquid which is substantially free of water and compounds which can yield water upon contact with the catalyst. Conditions of temperature and pressure which are desired for use in the chemical conversion that is to be carried out over the catalyst are then established in the fixed bed of solid phosphoric acid catalyst while it is immersed in the start-up fluid. The start-up fluid is then replaced by the feedstock that is to be used in the chemical conversion process, wherein the feedstock contains a minor amount of a hydrating agent which is comprised of at least one material selected from the group consisting of water and monohydric aliphatic alcohols which contain from 2 to 12 carbon atoms, and wherein the amount of the hydrating agent is effective to provide the desired level of catalyst hydration. A flow of the feedstock is then maintained through the catalyst bed under the conversion conditions that were previously established when the catalyst was immersed in the start-up fluid.

The start-up fluid is comprised of a hydrocarbon liquid which is substantially free of water and compounds which can yield water upon contact with the solid phosphoric acid catalyst. The start-up fluid is comprised of at least one hydrocarbon compound, and suitable hydrocarbon compounds can be selected from the group consisting of alkanes, cycloalkanes, olefins and aromatic compounds. In addition, the start-up fluid will preferably be a liquid at the conditions of temperature and pressure under which it is used in the practice of this invention. If desired, the start-up fluid can be a single substantially pure hydrocarbon compound, such as benzene, toluene, 1-butene or 2-methylbutane. Alternatively, it can be comprised of a mixture of hydrocarbons such as naphtha, reformate, kerosene, light cycle oil, a blend of light olefins, or a blend of any such materials. Highly satisfactory start-up fluids include reformates and the hydrocarbon feedstock to the conversion process itself which is substantially free of the hydrating agent.

The start-up fluid will have a distillation endpoint which is desirably below about 345° C. and is more preferably below about 300° C. For example, a preferred start-up fluid will boil in the range from about −50° to about 250° C. at atmospheric pressure, and a highly preferred start-up fluid will boil in the range from about 20° to about 250° C. at atmospheric pressure.

The fixed bed of solid phosphoric acid catalyst is brought to the desired conversion conditions of temperature and pressure while it is immersed in the start-up fluid. The start-up fluid is then replaced by the desired feedstock any time after the desired conversion conditions of temperature and pressure have been established in the fixed bed. This replacement is preferably carried out by displacing the start-up fluid by a flow of feedstock. Alternatively, the start-up fluid can be drained from the fixed bed of catalyst before the feedstock is contacted with the catalyst bed.

As previously stated, the feedstock contains a minor amount of a hydrating agent which is comprised of at least one material selected from the group consisting of water and monohydric aliphatic alcohols which contain from 2 to 12 carbon atoms, and wherein the amount of the hydrating agent is effective to provide the desired level of catalyst hydration. The concentration of hydrating agent in the feedstock will desirably be in the range from about 0.05 to about 0.80 mole percent, preferably from about 0.10 to about 0.50 mole percent, and more preferably from about 0.25 to about 0.30 mole percent. Ideally, the amount of the hydrating agent will be an amount which is capable of providing an amount of water which is just equal to the amount of water lost by the catalyst during the course of the conversion process.

Preferred hydrating agents include water, secondary alcohols and tertiary alcohols. Although the invention is not to be so limited, it is believed that the alcohols decompose upon contact with the solid phosphoric acid catalyst to yield water and decomposition products which include olefins that are produced by the acid catalyzed elimination of water from the alcohol. The secondary and tertiary alcohols are usually preferred over primary alcohols because they tend to decompose more readily upon contact with the solid phosphoric acid catalyst. Alcohols which contain from 3 to 5 carbon atoms are desirable hydrating agents, and such materials include 2-propanol, 2-butanol, 2-methyl-2-propanol, 2-pentanol, 3-pentanol, 3-methyl-2-butanol, and 2-methyl-2-butanol. 2-Propanol is a particularly satisfactory hydrating agent. When an alcohol is used as the hydrating agent or as a component of the hydrating agent and the hydrocarbon conversion involves the use of one or more olefins as reactants, it may be desirable to use an alcohol which has the same number of carbon atoms as one of the olefin reactants. Since a principal decomposition product from the alcohol will typically be an olefin which has the same number of carbon atoms as the alcohol, this olefin will then participate as a reactant in the hydrocarbon conversion process, and by-products will be minimized. For example, if 2-propanol is used as a hydrating agent for the polymerization of propene over a solid phosphoric acid catalyst, any propene produced by decomposition of the 2-propanol will be polymerized along with the propene in the feedstock.

Although water is a highly satisfactory hydrating agent, it is relatively insoluble in typical hydrocarbon feedstocks under ambient conditions of temperature and pressure. Accordingly, it is frequently not convenient to incorporate sufficient water in a hydrocarbon feedstock to provide a desired level of catalyst hydration. However, monohydric aliphatic alcohols which contain from 2 to 12 carbon atoms are ordinarily quite soluble in typical hydrocarbon feedstocks. Accordingly, these alcohols are very convenient for use as hydrating agents. A highly preferred embodiment of the invention involves the use of a hydrocarbon feedstock wherein the hydrating agent is comprised of a mixture of water and at least one alcohol which is selected from the group consisting of monohydric aliphatic alcohols which contain from 2 to 12 carbon atoms. Such a feedstock is conveniently prepared by adding one or more alcohols to the hydrocarbon components of the feedstock which contain water, and wherein the amount of water is insufficient to provide the desired level of catalyst hydration.

The process of this invention can be used in connection with the chemical conversion of any hydrocarbon feedstock which is carried out over a fixed bed of solid phosphoric acid catalyst. Such chemical conversions include, but are not limited to, olefin polymerization reactions and the alkylation of aromatic compounds with olefinic alkylating agents. Suitable olefins for use in such a process include, but are not limited to, cyclic olefins, substituted cyclic olefins, and olefins of Formula I wherein $R_1$ is a hydrocarbyl group and each $R_2$ is independently selected from the group consisting of hydrogen and hydrocarbyl groups. Preferably, $R_1$ is an alkyl group and each $R_2$ is independently selected from the group consisting of hydrogen

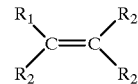

(I)

and alkyl groups. Examples of suitable cyclic olefins and substituted cyclic olefins include, but are not limited to, cyclopentene, 1-methylcyclopentene and cyclohexene. Examples of suitable olefins of the type of Formula I include, but are not limited to, propene, 2-methylpropene, 1-butene, 2-butene, 2-methyl-1-butene, 3-methyl-1-butene, 2-methyl-2-butene, 2,3-dimethyl-1-butene, 3,3-dimethyl-1-butene, 2,3-dimethyl-2-butene, 2-ethyl-1-butene, 1-pentene, 2-pentene, 2-methyl-1-pentene, 3-methyl-1-pentene, 4-methyl-1-pentene, 1-hexene, 2-hexene, and 3-hexene. Suitable olefins will desirably contain from 3 to 12 carbon atoms, preferred olefins will contain from 3 to 6 carbon atoms, and highly preferred olefins will contain from 3 to 4 carbon atoms.

When the process of this invention is used in connection with the alkylation of an aromatic compound with an olefinic alkylating agent, suitable aromatic compounds include all organic compounds of from 6 to 20 carbon atoms which contain aromatic functionality and can be alkylated by an olefin in the presence of a solid phosphoric acid catalyst. Such materials include both aromatic compounds and substituted aromatic compounds which carry one or more substituents. Aromatic hydrocarbons and hydrocarbyl-substituted aromatic hydrocarbons which contain from 6 to 10 carbon atoms are particularly suitable. In addition, mixtures of such materials can be used as a substrate. Examples of such materials include compounds of Formula II which contain from 6 to 20 carbon atoms where each R is independently selected from the group consisting of hydrogen and hydrocarbyl groups. However, preferred aromatic compounds are hydrocarbons which contain from 6 to 10 carbon atoms and are of Formula II where each R is independently selected from the group consisting of hydrogen and alkyl of from 1 to 3 carbon atoms. Benzene and toluene are particularly preferred.

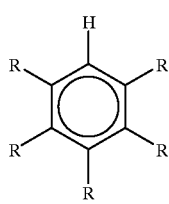

(II)

Aromatic compounds for use as alkylation substrates in the practice of this invention can be obtained from any desired source. However, in a petroleum refinery, catalytic cracking units, reformers and isomerization units are convenient sources of the aromatic compounds. For example, a light reformate can be used, and a typical material of this type will have a total aromatic content of about 35 vol. % and will contain about 10 vol. % of benzene.

In a highly preferred embodiment, the process of this invention can be used in connection with the conversion of a mixture of $C_3$ and $C_4$ olefins to gasoline blending stock by polymerization, and this type of product will be comprised of oligomers. In such an embodiment, the feedstock will be comprised of at least about 25% by volume of olefins. A typical olefin-containing feedstock to a polymerization unit for conversion to oligomers in the gasoline boiling range will comprise a mixture of propane, butane, 1-methylpropane, propene, 1-butene, 2-butene and 1-methylpropene, wherein the olefin concentration is in the range from about 35 to about 60 vol. %. However, it will be appreciated that the olefin-containing feedstock can have a variety of other compositions which include, but are not limited to, other olefins or olefin mixtures, other diluents, and the presence of a minor amount of aromatic compounds. In addition, olefin concentrations can be used which are outside this range.

In another highly preferred embodiment, the process of this invention can be used in connection with the conversion of a feedstock which comprises low molecular weight aromatic compounds in combination with $C_3$ and $C_4$ olefins to produce a product which is in the gasoline boiling point range and is useful as a gasoline blending stock. For example, the mole ratio of olefins to aromatic compounds can be in the range from about 1 to about 50, and preferably from about 1 to about 30. In such an embodiment, volatile low molecular weight aromatic compounds such as benzene, which are undesirable as gasoline components because of toxicity considerations, can be converted to less volatile materials, which are highly desirable gasoline components, by alkylation. For example, benzene and toluene can be converted to cumene and cymene, respectively, by monoalkylation with propene.

In those cases where the feedstock contains both olefins and aromatic compounds, alkylation of the aromatic compounds by the olefin or olefins in the feedstock will compete with olefin polymerization. As a result, both olefin polymers and alkylated aromatic compounds will be obtained as products, and the ratio of these products will be a function of the mole ratio of olefins to aromatic compounds in the feedstock. For example, when the mole ratio of olefins to aromatic compounds is about 1, the formation of products from alkylation of the aromatic compounds may predominate over the formation of olefin polymerization products. However, when the mole ratio of olefins to aromatic compounds is about 10, the formation of olefin polymers will typically predominate.

The hydrocarbon conversion process of this invention will typically be carried out with an olefin-containing feedstock. If desired, olefin-containing feedstocks for the conversion process of this invention can comprise a mixture of different olefins. Alternatively, the feedstock can be comprised of a single olefin. It will also be appreciated that the feedstock can comprise materials other than olefins, such as diluents which are substantially inert under the reaction conditions utilized in the conversion process. For example, the feedstock can contain substantial quantities of saturated hydrocarbons, such as normal paraffins, which will be relatively unreactive under the conditions of the conversion process of this invention. Indeed, a normal paraffin such as propane or butane can be used as a diluent and as a recycle material for managing the heat which is produced by exothermic olefin polymerization reactions or aromatic alkylation reactions.

Supported catalysts which are prepared by combining a phosphoric acid with a solid support are referred to herein as solid phosphoric acid catalysts, and any such catalyst can be used in the practice of this invention. A solid phosphoric acid catalyst is normally prepared by mixing a phosphoric acid, such as ortho-phosphoric acid, pyrophosphoric acid or triphosphoric acid, with a siliceous solid carrier to form a wet paste. This paste can be calcined and then crushed to yield catalyst particles, or the paste can be extruded or pelleted prior to calcining to produce more uniform catalyst particles. The carrier is typically a naturally occurring, porous silica-containing material such as kieselguhr, kaolin, infusorial earth or diatomaceous earth. A minor amount of various additives, such as mineral talc, fuller's earth and iron compounds, including iron oxide, can be added to the carrier to increase its strength and hardness. The combination of the carrier and the additives normally comprises about 15–30 wt. % of the catalyst, with the remainder being the phosphoric acid. However, the amount of phosphoric acid used in the manufacture of the catalyst can vary from about 8 to 80 wt. % of the catalyst. Solid phosphoric acid catalysts are available commercially, and such a material is available from UOP under the name SPA-2. This SPA-2 catalyst is a cylindrical extrudate having the following properties: (1) a nominal diameter of 4.75 mm; (2) a loaded density of 0.93 g/cm³; (3) a free phosphoric acid content, calculated as $P_2O_5$, of 16 to 20 wt. %; and (4) a nominal total phosphoric acid content, calculated as $P_2O_5$, of 60 wt. %. The preparation and properties of conventional solid phosphoric acid catalysts are set forth in U.S. Pat. No. 2,120,702 (Ipatieff et al.); U.S. Pat. No. 3,050,472 (Morrell); U.S. Pat. No. 3,050,473 (Morrell) and U.S. Pat. No. 3,132,109 (Morrell); and also in British Patent No. 863,539. These patents are incorporated herein by reference in their entirety.

The distribution of phosphoric acids in a solid phosphoric acid catalyst can be evaluated experimentally by titration of the "free $P_2O_5$" content of the catalyst, which consists of the acids that are easily leached from the catalyst when it is immersed in water. These easily leached acids are phosphoric acids which have a low degree of condensation, such as ortho-phosphoric acid and pyrophosphoric acid. The phosphoric acids which have a higher degree of condensation dissolve very slowly when the catalyst is immersed in water and, accordingly, are not measured by titration of the acids in the aqueous extract. Therefore, the amount of free $P_2O_5$ can be used as an indication of the distribution of phosphoric acids in a catalyst which has a given total $P_2O_5$ content.

The hydrocarbon conversion process of this invention is carried out in a fixed bed of the solid phosphoric acid catalyst. If desired, the catalyst can be located in a chamber reactor or a tubular reactor. In a tubular reactor, the catalyst is contained in a multiplicity of tubes which are surrounded by a circulating cooling medium. These tubes will typically have an internal diameter of from about 5 cm to about 15 cm, although other diameters can also be used. A tubular reactor is frequently preferable to a chamber reactor because it permits a closer control of the reaction temperature and can be easily constructed for high pressure operation. Ordinarily, a plurality of reactors will be used. For example, an olefin polymerization unit employing tubular reactors can have as many as eight or more reactors. The heat produced by the exothermic olefin conversion reactions can be controlled in a chamber reactor by using a saturated hydrocarbon as a recycle from reactor effluent to reactor feedstock and/or as a quench between multiple catalyst beds within the reactor. The temperature in tubular reactors is typically controlled by water or oil circulation around the reactor tubes.

In the practice of the process of this invention, the feedstock is contacted with the solid phosphoric acid catalyst at a temperature, pressure and period of time which are effective to result in conversion of at least a portion of the reactants in the feedstock to the desired products. Desirably, the contacting temperature will be in excess of about 50° C., preferably in excess of 100° C., and more preferably in excess of 125° C. The contacting will generally be carried out at a temperature in the range from about 50° to about 350° C., preferably from about 100° to about 350° C., and more preferably from about 125° to about 250° C. It will be appreciated, of course, that the optimum temperature will be a function of the specific reactants employed and their concentration in the feedstock. For example, for the polymerization of propene and/or $C_4$ olefins, the reaction temperature will usually be in the range from about 150° about 250° C.

In the practice of the process of this invention, the feedstock can be contacted with the solid phosphoric acid catalyst at any suitable pressure. However, pressures in the range from about 0.01 to about 200 atmospheres are desirable, and a pressure in the range from about 1 to about 100 atmospheres is preferred. For example, when a typical solid phosphoric acid catalyst is used for the conversion of propene and/or $C_4$ olefins to gasoline blending stock, the pressure will usually be in the range from about 20 to about 90 atmospheres.

Deactivation of a solid phosphoric acid catalyst during use to catalyze either the polymerization of olefins or the alkylation of aromatic compounds with olefins is often believed to be a result of the formation of high boiling polymers as by-products. These by-products can remain on the catalyst and undergo further conversion to even higher molecular weight polymers which resemble heavy tars and, in some cases, even have the appearance of a coke-like material. These materials can coat the catalyst particles and plug pores in the catalyst, thereby causing catalyst deactivation. Accordingly, it is frequently desirable to carry out the process of this invention at a pressure which is sufficient to maintain a liquid phase of hydrocarbon in contact with the catalyst. This liquid hydrocarbon phase can keep the high molecular weight polymers or tar washed off the catalyst and thereby prolong the catalyst life.

EXAMPLE 1

A fresh 7.0 g portion of solid phosphoric acid catalyst on kieselguhr (obtained from UOP under the name SPA-2) was loaded into a tubular, stainless steel reactor of 0.95 cm internal diameter. The catalyst was reported by the supplier to have a free phosphoric acid content (as $P_2O_5$) of 16 to 20 wt. % and a total phosphoric acid content (as $P_2O_5$) of 60 wt. %.

The fixed bed of solid phosphoric acid catalyst was used as a catalyst for the conversion of a mixture of $C_3/C_4$ olefins and light aromatic hydrocarbons to higher molecular weight products. This aromatics-containing feedstock consisted of a mixture of a light reformate with a hydrated olefin-containing $C_3/C_4$ stream (the olefin-containing $C_3/C_4$ stream is hereinafter referred to as the "$C_3/C_4$ feedstock component"), and the ratio of the light reformate to hydrated $C_3/C_4$ feedstock component was 1:10 on a volume basis. The analysis of these materials is set forth in Tables I and II, respectively.

The fixed bed of solid phosphoric acid was put into service using a conventional start-up procedure. This involved purging the reactor with nitrogen and preheating the catalyst bed to 107° C. The reactor was then filled with the aromatics-containing feedstock and brought to a pressure of 81.7 atm over a period of 4 hours.

TABLE I

Light Reformate Composition.

| Component | Amount, Vol. % |
|---|---|
| Olefins | 1 |
| Aromatics (including benzene) | 34 |
| Saturated Hydrocarbons | 65 |
| Benzene | 10 |

TABLE II

Composition of Hydrated $C_3/C_4$ Feedstock Component.

| Component | Amount | |
|---|---|---|
| Water | 1000 | ppm |
| Propane | 18 | vol. % |
| Propene | 22 | vol. % |
| n-Butane | 15 | vol. % |
| 2-Methylpropane | 20 | vol. % |
| $C_4$-Olefins | 25 | vol. % |

Finally, the reactor was heated to the desired process temperature of 204° C., and a flow of aromatics-containing feedstock into the reactor was established at a level corresponding to 2.0 LHSV of the hydrated $C_3/C_4$ feedstock component and 0.2 LHSV of the light reformate. After the reactor had been continuously operated under these conditions of temperature, pressure and flow rate for a period of 5 days, the aromatics-containing feedstock was replaced by a standardized polymerization feedstock at a flow rate of 2.0 LHSV while the reactor temperature and pressure were maintained at 204° C. and 81.7 atm, respectively. The standardized polymerization feedstock was obtained from Matheson Gas Products, and it was utilized for the purpose of evaluating the catalyst activity. The standardized polymerization feedstock was free of aromatics and contained 27% propene, 18% $C_4$ olefins, 55% propane, and 1500 ppm by weight of 2-propanol as a hydrating agent.

The activity constant of the solid phosphoric acid catalyst in the reactor and the amount of $C_3$ and $C_4$ olefins converted to higher molecular weight products upon passage through the reactor were then measured as a function of time using the standardized polymerization feedstock. For the purpose of these measurements, the combined conversion of $C_3$ and $C_4$ olefins is defined as X, and the activity constant k=LHSV{ln[1/(1−X)]}. These results are set forth in Table III, and they show that the solid phosphoric acid catalyst does not reach optimum activity for more than 10 days when the conventional start up procedure of this Example I is used.

EXAMPLE II

Example I was repeated except that the reactor was filled with anhydrous light reformate during the start-up procedure rather than the mixture of the hydrated $C_3/C_4$ feedstock component with light reformate that was used in Example I. As before, the start-up procedure of this Example II involved an initial purge the reactor with nitrogen and preheating the catalyst bed to 107° C. The reactor was then filled with an anhydrous light reformate (the analysis of this material is set forth in Table I, and it is the same light reformate that was used as a component of the aromatics-containing feedstock in Example I), and the reactor was brought to a pressure of 81.7 atm over a period of 4 hours. Finally, the reactor was heated to the desired process temperature of 204° C., and a flow of aromatics-containing feedstock into the reactor was established at a level corresponding to 2.0 LHSV of the hydrated $C_3/C_4$ feedstock component and 0.2 LHSV of the light reformate (the aromatics-containing

TABLE III

Results from Conventional Start-Up Procedure of Example I.

| Time After Initiation of Start-Up, hr. | Activity Constant of Catalyst, k | Conversion of $C_3$ and $C_4$ Olefins, % |
| --- | --- | --- |
| 137.2 | 5.1 | 92.3 |
| 161.2 | 5.7 | 94.3 |
| 185.2 | 5.7 | 94.3 |
| 209.2 | 6.0 | 95.1 |
| 233.2 | 6.2 | 95.6 |
| 257.2 | 6.3 | 95.7 |
| 281.2 | 6.4 | 96.0 |
| 305.2 | 6.4 | 95.8 |
| 329.2 | 7.1 | 97.1 |
| 353.2 | 6.8 | 96.6 |
| 377.2 | 7.4 | 97.6 |
| 401.2 | 7.0 | 97.0 |
| 424.8 | 6.8 | 96.7 |
| 449.2 | 7.3 | 97.4 | feedstock was identical to that which is described in Example I). After the reactor had been continuously operated under these conditions of temperature, pressure and flow rate for a period of 5 days, the aromatics-containing feedstock was replaced by the standardized polymerization feedstock of Example I at a flow rate of 2.0 LHSV while the reactor temperature and pressure were maintained at 204° C. and 81.7 atm, respectively.

The activity constant of the solid phosphoric acid catalyst in the reactor and the amount of $C_3$ and $C_4$ olefins converted to higher molecular weight products upon passage through the reactor were then measured as a function of time using the standardized polymerization feedstock. These results are set forth in Table IV, and they show that the catalyst was 40% more active after 161 hr and 15% more active after 305 hr relative to the catalyst activity obtained using the conventional start-up procedure of Example I.

TABLE IV

Results from Start-Up Procedure of Example II Using Anhydrous Light Reformate as a Start-Up Fluid.

| Time After Initiation of Start-Up, hr. | Activity Constant of Catalyst, k | Conversion of $C_3$ and $C_4$ Olefins, % |
| --- | --- | --- |
| 161.0 | 7.8 | 97.9 |
| 185.0 | 8.0 | 98.1 |
| 209.0 | 8.1 | 98.2 |
| 233.2 | 8.2 | 98.3 |
| 256.5 | 8.2 | 98.4 |
| 281.0 | 8.3 | 98.4 |
| 305.2 | 8.3 | 98.4 |

EXAMPLE III

Example I was repeated except that the reactor was filled with anhydrous $C_3/C_4$ feedstock component during the start-up procedure rather than the mixture of the hydrated $C_3/C_4$ feedstock component with light reformate that was used in Example I. As before, the start-up procedure of this Example III involved an initial purge of the reactor with nitrogen and preheating the catalyst bed to 107° C. The reactor was then filled with anhydrous $C_3/C_4$ feedstock component (this material was identical to the hydrated $C_3/C_4$ feedstock component used as a feedstock component in Example I, except that it was free of water), and the reactor was brought to a pressure of 81.7 atm over a period of 4 hours. Finally, the reactor was heated to the desired process temperature of 204° C., and a flow of aromatics-containing feedstock into the reactor was established at a level corresponding to 2.0 LHSV of the hydrated $C_3/C_4$ feedstock component and 0.2 LHSV of the light reformate (the aromatics-containing feedstock was identical to that which is described in Example I). After the reactor had been continuously operated under these conditions of temperature, pressure and flow rate for a period of 5 days, the feedstock was replaced by the standardized polymerization feedstock of Example I at a flow rate of 2.0 LHSV while the reactor temperature and pressure were maintained at 204° C. and 81.7 atm, respectively.

The activity constant of the solid phosphoric acid catalyst in the reactor and the amount of $C_3$ and $C_4$ olefins converted to higher molecular weight products upon passage through the reactor were then measured as a function of time using the standardized polymerization feedstock. These results, which are set forth in Table V, are comparable to those obtained in Example II and are much superior to the results obtained using the conventional start-up procedure of Example I.

TABLE V

Results from Start-Up Procedure of Example III Using Anhydrous $C_3/C_4$ Feedstock Component as a Start-Up Fluid.

| Time After Initiation of Start-Up, hr. | Activity Constant of Catalyst, k | Conversion of $C_3$ and $C_4$ Olefins, % |
| --- | --- | --- |
| 161.0 | 7.9 | 98.2 |
| 184.8 | 8.0 | 98.3 |

TABLE V-continued

Results from Start-Up Procedure of
Example III Using Anhydrous $C_3/C_4$
Feedstock Component as a Start-Up Fluid.

| Time After Initiation of Start-Up, hr. | Activity Constant of Catalyst, k | Conversion of $C_3$ and $C_4$ Olefins, % |
| --- | --- | --- |
| 209.0 | 8.1 | 98.4 |
| 232.0 | 8.2 | 98.4 |
| 256.5 | 8.2 | 98.5 |
| 281.0 | 8.2 | 98.5 |
| 305.2 | 8.2 | 98.5 |
| 329.0 | 8.2 | 98.5 |
| 353.0 | 8.2 | 98.5 |

We claim:

1. A process for initiating and maintaining the flow of a feedstock through a fixed bed of solid phosphoric acid catalyst, wherein said feedstock is comprised of an olefin-containing hydrocarbon stream in combination with a hydrating agent which comprises:
   (a) immersing the bed of catalyst in a start-up fluid, wherein said start-up fluid consists essentially of a hydrocarbon liquid;
   (b) establishing desired conditions of temperature and pressure in the catalyst bed while the catalyst bed is immersed in the start-up fluid, wherein said temperature is in the range from about 50° C. to about 350° C. and said pressure is in the range from about 1 to about 100 atmospheres;
   (c) replacing the start-up fluid in the catalyst bed with the feedstock under said conditions of temperature and pressure, wherein the feedstock contains a minor amount of a hydrating agent which is comprised of at least one material selected from the group consisting of water and monohydric aliphatic alcohols which contain from 2 to 12 carbon atoms, and wherein the amount of said hydrating agent is effective to provide a desired level of catalyst hydration; and
   (d) maintaining a flow of said feedstock through the catalyst bed under said conditions of temperature and pressure.

2. The process of claim 1 wherein the concentration of said hydrating agent in the feedstock is in the range from about 0.05 to about 0.80 mole percent.

3. The process of claim 1 wherein the feedstock is comprised of at least 25% by volume of olefins.

4. The process of claim 1 wherein the feedstock additionally contains saturated hydrocarbons.

5. The process of claim 1 wherein the feedstock is comprised of olefins and aromatic hydrocarbons in combination with a hydrating agent.

6. The process of claim 5 wherein the mole ratio of olefins to aromatic hydrocarbons is in the range from about 1 to about 50.

7. The process of claim 5 wherein the feedstock additionally contains saturated hydrocarbons.

8. The process of claim 1 wherein the start-up fluid is comprised of a material which is selected from the group consisting of naphthas, reformates, kerosenes, light cycle oils, blends of light olefins, and blends thereof.

9. The process of claim 1 which additionally comprises catalyzing chemical modification of said olefin-containing feedstock in the catalyst bed, wherein said desired conditions of temperature and pressure are effective to result in said modification, and wherein said modification is the result of at least one process selected from the group consisting of olefin polymerization and the alkylation of aromatic compounds with olefins.

10. The process of claim 1 wherein the start-up fluid is comprised of said feedstock which is free of said hydrating agent.

11. An olefin polymerization process carried out over a fixed bed of solid phosphoric acid catalyst which comprises:
   (a) immersing the bed of catalyst in a start-up fluid, wherein said start-up fluid consists essentially of a hydrocarbon liquid;
   (b) establishing olefin polymerization conditions of temperature and pressure in the catalyst bed while the catalyst bed is immersed in the start-up fluid;
   (c) replacing the start-up fluid with an olefin-containing feedstock and passing said feedstock through the catalyst bed under said polymerization conditions, wherein the feedstock contains a minor amount of a hydrating agent which is comprised of at least one material selected from the group consisting of water and monohydric aliphatic alcohols which contain from 2 to 12 carbon atoms, and wherein the amount of said hydrating agent is effective to provide a desired level of catalyst hydration; and
   (d) maintaining the flow of said feedstock through the catalyst bed under said polymerization conditions.

12. The process of claim 11 wherein the concentration of said hydrating agent in the feedstock is in the range from about 0.05 to about 0.80 mole percent.

13. The process of claim 12 wherein the concentration of said hydrating agent in the feedstock is in the range from about 0.10 to about 0.50 mole percent.

14. The process of claim 11 wherein said start-up fluid has a distillation endpoint which is below about 345° C.

15. The process of claim 11 wherein said start-up fluid is comprised of a material which is selected from the group consisting of naphthas, reformates, kerosenes, light cycle oils, blends of light olefins, and blends thereof.

16. The process of claim 15 wherein said start-up fluid is comprised of a reformate.

17. The process of claim 11 wherein said start-up fluid is comprised of said feedstock which is free of said hydrating agent.

18. The process of claim 11 wherein the hydrating agent is comprised of at least one material selected from the group consisting of water and 2-propanol.

19. The process of claim 11 wherein the feedstock is comprised of at least 25% by volume of olefins.

20. The process of claim 11 wherein the feedstock is comprised of at least one olefin which is selected from the group consisting of olefins which contain from 3 to 12 carbon atoms.

21. The process of claim 20 wherein the feedstock is comprised of at least one olefin which is selected from the group consisting of olefins which contain from 3 to 6 carbon atoms.

22. The process of claim 20 wherein the feedstock is comprised of at least one olefin which is selected from the group consisting of olefins which contain from 3 to 4 carbon atoms.

23. The process of claim 11 wherein the product from the polymerization of the olefins in said feedstock is comprised of oligomers.

24. The process of claim 11 wherein the olefin polymerization conditions include a temperature which is in the range from about 125° to about 250° C.

25. The process of claim 11 wherein the olefin polymerization conditions include a pressure which is effective to maintain a liquid phase of hydrocarbon in contact with the catalyst when the feedstock is passed through the catalyst bed.

* * * * *